United States Patent
Wan et al.

(10) Patent No.: US 11,376,299 B2
(45) Date of Patent: Jul. 5, 2022

(54) LILAC GINKGO BRICK TEA AND METHOD OF PREPARING THE SAME

(71) Applicants: Jia Wan, Xi'an (CN); Chunchun Kong, Xi'an (CN); Chengyuan Liang, Xi'an (CN); Nan Hui, Xi'an (CN); Chunyang Shi, Xi'an (CN); Han Li, Xi'an (CN); Bin Tian, Xi'an (CN); Gennian Mao, Xi'an (CN); Qianqian Zhao, Xi'an (CN); Qiao Zeng, Xi'an (CN)

(72) Inventors: Jia Wan, Xi'an (CN); Chunchun Kong, Xi'an (CN); Chengyuan Liang, Xi'an (CN); Nan Hui, Xi'an (CN); Chunyang Shi, Xi'an (CN); Han Li, Xi'an (CN); Bin Tian, Xi'an (CN); Gennian Mao, Xi'an (CN); Qianqian Zhao, Xi'an (CN); Qiao Zeng, Xi'an (CN)

(73) Assignee: XI'AN KANGYUANSHENG BIOMEDICAL TECHNOLOGY CO., LTD., Xi'an (CN)

( * ) Notice: Subject to any disclaimer, the term of this patent is extended or adjusted under 35 U.S.C. 154(b) by 211 days.

(21) Appl. No.: 16/658,130

(22) Filed: Oct. 20, 2019

(65) Prior Publication Data
US 2020/0353027 A1 Nov. 12, 2020

(30) Foreign Application Priority Data

May 6, 2019 (CN) .......................... 201910369323.0

(51) Int. Cl.
| | |
|---|---|
| *A61K 36/63* | (2006.01) |
| *A61K 36/16* | (2006.01) |
| *A61K 36/82* | (2006.01) |
| *A61K 9/00* | (2006.01) |

(52) U.S. Cl.
CPC ............ *A61K 36/63* (2013.01); *A61K 9/0095* (2013.01); *A61K 36/16* (2013.01); *A61K 36/82* (2013.01)

(58) Field of Classification Search
None
See application file for complete search history.

(56) References Cited

FOREIGN PATENT DOCUMENTS

CN 109198095 A * 1/2019

OTHER PUBLICATIONS

Planty Delights. May 11, 2017. Lilac blossoms and leaves- find out three easy ways to use them. Datasheet [online]. Retrieved on Jul. 12, 2021. Downloaded from the internet: <https://plantydelights.com/lilac-blossoms-leaves-three-easy-ways-use/> pp. 1-13. specif, pp. 2, 3.*
Noort, L. Dec. 2014. 1. 5 Reasons to grow Sanguisorba minor. Datasheet [online]. Sow and So. Retrieved on Jul. 12, 2021. Downloaded from the internet: <https://www.sowandso.com/5-reasons-grow-sanguisorba-minor/> pp. 1-8. specif, pp. 3, 4.*
EngMT—Tang, Li. Compound ginkgo fuzhuan brick tea and production method thereof. Chinese Patent Application Publication No. CN109198095A; Pub. Date: Jan. 15, 2019, pp. 1-14. specif, pp. 1, 2, 4, 6, 7.*
Liang, J. et al. 2013. Extracts of the medicinal herb Sanguisorba officinalis inhibit the entry of human immunodeficiency virus-1. Journal of Food and Drug Analysis 21: S52-S58. specif, pp. S52, S53.*
Wikipedia.Sanguisorba. Datasheet [online]. Retrieved on Jan. 26, 2022. Downloaded from the internet: <en.wikipedia.org/wiki/Sanguisorba> Page last edited: Dec. 16, 2021; pp. 1-3.*
Valencia, E. et al. 2016. Functional leaf and size traits determine photosynthetic response of 10 dryland species to warming. Journal of Plant Ecology 9(6): 773-783; specif. pg 773.*
Gardenia.Sanguisorba officinalis. Datasheet [online]. Retrieved on Jan. 26, 2022. Downloaded from the internet: <https://www.gardenia.net/plants/sanguisorba-officinalis> pp. 1-9; specif. pp. 1-3.*
Annie's Remedy. Salad Burnet Sanguisorba minor. Copyright 2005-2018 Annie's Remedy. Retrieved on Jul. 12, 2021. Downloaded from the internet: <https://www.anniesremedy.com/sanguisorba-minor-salad-burnet.php> pp. 1-6; specif. pp. 1-3.*

* cited by examiner

*Primary Examiner* — Olivia M. Wise
*Assistant Examiner* — Sharon M. Papciak

(57) ABSTRACT

A method of preparing a Lilac *Ginkgo* Brick Tea includes the following steps: (1) mixing and drying fresh Lilac leaves and *Ginkgo* leaves to obtain a Lilac *Ginkgo* Tea; (2) fermenting the Lilac *Ginkgo* Tea to obtain a Fermented Lilac *Ginkgo* Tea; (3) mixing the Fermented Lilac *Ginkgo* Tea with a black tea to obtain a Fermented Lilac *Ginkgo* Tea Mixture; and (4) processing the Fermented Lilac *Ginkgo* Tea Mixture to obtain the Lilac *Ginkgo* Brick Tea.

1 Claim, No Drawings

LILAC GINKGO BRICK TEA AND METHOD OF PREPARING THE SAME

The present invention claims priority to Chinese Application No.: 201910369323.0, filed May 6, 2019, which is incorporated by reference for all purposes as if fully set forth herein.

FIELD OF THE INVENTION

The present invention relates to a method of preparing a Lilac *Ginkgo* Brick Tea. The Lilac *Ginkgo* Brick Tea has lipid lowering and liver protection activities.

BACKGROUND OF THE INVENTION

Lilac (*Syringa vulgaris*) is a flowering plant in the olive family Oleaceae. It is mainly cultivated as a horticultural ornamental plant, and its flower can be used to extract aromatic oil. The leaves and fruits of Lilac have some medicinal use, and main ingredients include phenylpropanoids, iridoids, sulphonic iridoids, flavonoids and saponins, such as eugenol, syringin and oleuropein.

*Ginkgo* (*Ginkgo biloba*) is the only living species in the division Ginkgophyta. It is found in fossils dating back 270 million years. *Ginkgo* has been widely cultivated, and has various uses in traditional medicine and as a source of food. The leaves and fruits of *Ginkgo* are rich in various nutrients, such as protein, amino acid, minerals and vitamins. Existing *Ginkgo* tea is a single form of tea that is simply processed into strips or flakes using *Ginkgo* leaves or deep-processed ultrafine powder. Regardless of the physical shape, the *Ginkgo* tea is coarse and yellow, and must be boiled for 2-3 minutes or brewed with boiling water for 15 minutes before drinking. The taste of the *Ginkgo* tea is bitter and sour.

Fermented Tea (also known as post-fermented tea or dark tea) is a class of tea that has undergone microbial fermentation. The tea leaves become darker with oxidation during the fermentation process. The fermentation affects the smell of the tea and reduces astringency and bitterness. The microbes may also produce metabolites with health benefits.

The present invention uses Lilac leaves and *Ginkgo* leaves to prepare fermented tea. Fermentation can reduce the bitter taste of Lilac leaves and *Ginkgo* leaves while producing beneficial metabolites, and the resulted fermented tea has lipid-lowering and liver-protecting effects.

SUMMARY OF THE INVENTION

In one embodiment, the present invention provides a method of preparing a Lilac *Ginkgo* Brick Tea. The method includes the following steps: (1) mixing and drying fresh Lilac leaves and *Ginkgo* leaves to obtain a Lilac *Ginkgo* Tea; (2) fermenting the Lilac *Ginkgo* Tea to obtain a Fermented Lilac *Ginkgo* Tea; (3) mixing the Fermented Lilac *Ginkgo* Tea with a black tea to obtain a Fermented Lilac *Ginkgo* Tea Mixture; and (4) processing the Fermented Lilac *Ginkgo* Tea Mixture to obtain the Lilac *Ginkgo* Brick Tea.

In another embodiment, step (1) mixing and drying fresh Lilac leaves and *Ginkgo* leaves includes: collecting fresh Lilac leaves and *Ginkgo* leaves in a weight ratio of 7:3; washing the Lilac leaves and the *Ginkgo* leaves with water 2-3 times; drying the Lilac leaves and the *Ginkgo* leaves at room temperature for 3-6 hours; cutting the Lilac leaves and the *Ginkgo* leaves into strips with a width of 3-5 mm; drying the Lilac leaves at 130-150° C. for 4-7 minutes, rolling the Lilac leaves for 20-40 minutes, and drying the Lilac leaves at 110-120° C. for 1-3 hours; drying the *Ginkgo* leaves at 220-250° C. for 10-15 minutes, rolling the *Ginkgo* leaves for 20-40 minutes, and drying the *Ginkgo* leaves at 110-120° C. for 1-3 hours; and mixing the Lilac leaves and the leaves *Ginkgo*.

In another embodiment, step (2) fermenting the Lilac *Ginkgo* Tea includes: spraying the spores of *Eurotium cristatum* in a ratio of $(0.5-1) \times 10^7$ spores per kilogram of the Lilac *Ginkgo* Tea; piling the Lilac *Ginkgo* Tea at 20-30° C. and 65-85% relative humidity for 30-40 hours; and drying the Lilac *Ginkgo* Tea at 20-30° C. for 2-5 hours.

In another embodiment, in step (3), the Fermented Lilac *Ginkgo* Tea has a weight ratio of 40-90% and the black tea has a weight ratio of 10-60%.

In another embodiment, step (4) processing the Fermented Lilac *Ginkgo* Tea Mixture includes: taking a portion of the Fermented Lilac *Ginkgo* Tea Mixture, boiling in water to obtain an extract; adding the extract to the remaining Fermented Lilac *Ginkgo* Tea Mixture; piling the Fermented Lilac *Ginkgo* Tea Mixture at 20-30° C. and 40-60% relative humidity for 1-3 hours; steaming the Fermented Lilac *Ginkgo* Tea Mixture for 8-12 seconds; spreading the spores of *Eurotium cristatum* in a ratio of $(3-6) \times 10^6$ spores per kilogram of the Fermented Lilac *Ginkgo* Tea Mixture; pressing the Fermented Lilac *Ginkgo* Tea Mixture into brick shape; and curing the Fermented Lilac *Ginkgo* Tea Mixture at 20-25° C. and 65-80% relative humidity for 4 days and at 25-30° C. and 45-65% relative humidity for 10 days.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

The present invention uses Lilac leaves, *Ginkgo* leaves, and blank tea to make Lilac *Ginkgo* Brick Tea. The bitterness of *Ginkgo* tea is reduced by fermentation. Lilac *Ginkgo* Brick Tea has higher contents of active ingredients, such as saponins, flavonoids, and polysaccharides than traditional brick tea.

Reference will now be made in detail to embodiments of the present invention, example of which is illustrated.

Fresh and health Lilac leaves and *Ginkgo* leaves were collected during months of July to September. Lilac *Ginkgo* Brick Tea with lipid lowering and liver protection activities was prepared in accordance with the following steps.

(1) Preparation of Lilac *Ginkgo* Tea: Fresh Lilac leaves and *Ginkgo* leaves were immersed in mountain spring water, rinsed 2-3 times, drained and placed in bamboo rafts (about 1.5 cm thick), dried in a cool dry place for 3-6 hours, placed in a slicer, cut into 3-5 mm strips. The Lilac leaves were dried in a tea dryer at 130-150° C. for 4-7 minutes. Fixation of the Lilac leaves was complete, and the water content was about 40-55%. The Lilac leaves was then rolled in a tea roller for 20-40 minutes, and dried at 110-120° C. for 1-3 hours. The *Ginkgo* leaves were dried in a tea dryer at 220-250° C. for 10-15 minutes, and then rolled in a tea roller for 20-40 minutes and dried at 110-120° C. for 1-3 hour. The Lilac leaves and *Ginkgo* leaves were then mixed in a weight ratio of 7:3 to make the Lilac *Ginkgo* Tea.

(2) Piling the Lilac *Ginkgo* Tea to remove bitterness: The spores of *Eurotium cristatum* ($1 \times 10^6$/mL suspension or $1 \times 10^6$/g powder) were sprayed onto the Lilac *Ginkgo* Tea in a ratio of $(5-10) \times 10^6$ spores per kilogram of the Lilac *Ginkgo* Tea and mixed well (water content: about 45-55%). The Lilac *Ginkgo* Tea was piled at 20-35° C. and 65-85% relative humidity for 30-40 hours and dried in a tea dryer at 100-120° C. for 2-5 hours to prepare a Fermented Lilac *Ginkgo* Tea.

(3) Mixing the Fermented Lilac *Ginkgo* Tea with black tea: The Fermented Lilac *Ginkgo* Tea and a black tea were mixed in a weight ratio of 40-90%:10-60% to make Fermented Lilac *Ginkgo* Tea Mixture (100 kg).

(4) Preparation of the Lilac *Ginkgo* Brick Tea:

A portion of the Fermented Lilac *Ginkgo* Tea Mixture (1 kg) was boiled in water (35-65 kg) for 30-40 minutes and filtered to obtain an extract (30-40 kg). The extract was added to the remaining Fermented Lilac *Ginkgo* Tea Mixture. The Fermented Lilac *Ginkgo* Tea Mixture was piled at 20-30° C. and 40-60% relative humidity for 1-3 hours, and then steamed for 8-12 seconds. The spores of *Eurotium cristatum* ($1\times10^6$/mL suspension or $1\times10^6$/g powder) were sprayed onto the Fermented Lilac *Ginkgo* Tea Mixture in a ratio of $(3-6)\times10^6$ spores per kilogram of the Fermented Lilac *Ginkgo* Tea Mixture. The Fermented Lilac *Ginkgo* Tea Mixture was pressed into brick shape in a press mold. After cooling down, the Fermented Lilac *Ginkgo* Tea Mixture was cured in a curing room under the following conditions: days 1-4, at 20-25° C. and 65-80% relative humidity; days 5-14, at 25-30° C. and 45-65% relative humidity. The relative humidity was preferably decreased gradually. After curing, the mixture was slowly dried in a dry and ventilated environment, and the water content of the mixture was reduced to about 7%. Lilac *Ginkgo* Brick Tea was obtained.

Table 1 shows the operation details of each step in Examples 1-4:

TABLE 1

| Steps | Operation Details | Example 1 | Example 2 | Example 3 | Example 4 |
|---|---|---|---|---|---|
| Preparation of Lilac *Ginkgo* Tea | Washing leaves (times) | 2 | 3 | 2 | 3 |
| | Drying leaves (hours) | 4 | 6 | 3 | 5 |
| | Leaf strip size (mm) | 4 | 3 | 5 | 4 |
| | Lilac leaves drying temp. (° C.) | 140 | 130 | 150 | 135 |
| | Ginkgo leaves drying temp. (° C.) | 235 | 220 | 250 | 230 |
| | Lilac leaves drying time (min) | 5 | 6 | 4 | 7 |
| | Ginkgo leaves drying time (min) | 10 | 11 | 12 | 15 |
| | Lilac leaves water content (%) | 45 | 55 | 40 | 45 |
| | Leaves rolling time (min) | 30 | 40 | 20 | 35 |
| | Leaves drying temperature (° C.) | 110 | 115 | 120 | 115 |
| | Leaves drying time (hour) | 2 | 3 | 1 | 2 |
| Piling and removing bitterness | Spores of *Eurotium cristatum* per Kg | $10 \times 10^6$ | $5 \times 10^6$ | $7 \times 10^6$ | $8 \times 10^6$ |
| | Applying method | Spraying | Spraying | Spraying | Dusting |
| | Piling water content (%) | 48 | 45 | 55 | 50 |
| | Piling temperature (° C.) | 28 | 35 | 25 | 30 |
| | Piling relative humidity (%) | 70 | 85 | 65 | 75 |
| | Piling time (hour) | 35 | 30 | 40 | 30 |
| | Drying temperature (° C.) | 110 | 115 | 120 | 110 |
| | Drying time (hour) | 3 | 4 | 2 | 5 |
| Mixing | Blank tea (wt %) | 20 | 60 | 10 | 40 |
| | Fermented Lilac Ginkgo Tea (wt %) | 80 | 40 | 90 | 60 |
| Preparation of the Lilac Ginkgo Brick Tea | Extraction water (kg) per 1 kg | 50 | 35 | 45 | 65 |
| | Extraction boiling time (min) | 30 | 35 | 40 | 35 |
| | Extract (kg) per 100 kg | 35 | 30 | 35 | 40 |
| | Piling temperature (° C.) | 25 | 20 | 30 | 25 |
| | Piling relative humidity (%) | 50 | 45 | 60 | 55 |
| | Piling time (hour) | 2 | 3 | 1 | 2 |
| | Steaming time (sec) | 10 | 8 | 12 | 11 |
| | Spores of *Eurotium cristatum* per Kg | $5 \times 10^6$ | $3 \times 10^6$ | $6 \times 10^6$ | $4 \times 10^6$ |
| | Applying method | Spraying | Spaying | Spraying | Dusting |
| | Days 1-4, curing temp. (° C.) | 22 | 25 | 20 | 24 |
| | Days 1-4, relative humidity (%) | 75 | 80 | 65 | 70 |
| | Days 5-14, curing temperature (25-30° C.) | | | | |
| | Days 5-8, curing temp. (° C.) | 25 | 26 | 27 | 25 |
| | Days 9-14, curing temp. (° C.) | 28 | 29 | 28 | 30 |
| | Days 5-14, curing relative humidity (45-65%) | | | | |
| | Days 5-8, relative humidity (%) | 65 | 65 | 65 | 65 |
| | Days 9-10, relative humidity (%) | 60 | 60 | 60 | 60 |
| | Days 11-12, relative humidity (%) | 55 | 55 | 55 | 55 |
| | Days 13-14, relative humidity (%) | 45 | 45 | 45 | 45 |

Example 1

Fresh Lilac leaves and *Ginkgo* leaves were immersed in mountain spring water, rinsed 2 times, drained and placed in bamboo rafts (about 1.5 cm thick), dried in a cool dry place for 4 hours, placed in a slicer, cut into 4 mm strips. The Lilac leaves were dried in a tea dryer at 140° C. for 5 minutes. Fixation of the Lilac leaves was complete, and the water content was about 45%. The *Ginkgo* leaves were dried in a tea dryer at 235° C. for 10 minutes. The Lilac leaves and *Ginkgo* leaves were then mixed in a weight ratio of 7:3, rolled in a tea roller for 30 minutes, and dried in a tea dryer at 110° C. for 2 hours to make the Lilac *Ginkgo* Tea.

The Lilac *Ginkgo* Tea was piled to remove bitterness. The spores of *Eurotium cristatum* ($1\times10^6$/mL suspension) were sprayed onto the Lilac *Ginkgo* Tea in a ratio of 10 mL suspension per kilogram of the Lilac *Ginkgo* Tea and mixed well (water content: about 48%). The Lilac *Ginkgo* Tea was piled at 28° C. and 70% relative humidity for 35 hours and dried in a tea dryer at 110° C. for 3 hours to prepare a Fermented Lilac *Ginkgo* Tea.

Black tea (20 kg) and Fermented Lilac *Ginkgo* Tea (80 kg) were mixed to make Fermented Lilac *Ginkgo* Tea Mixture (100 kg). 1 kg of Fermented Lilac *Ginkgo* Tea Mixture was added to 50 kg river water, boiled for 30 min, and filtered and cooled to obtain an extract. 35 kg of extract was added to the remaining Fermented Lilac *Ginkgo* Tea Mixture. The Fermented Lilac *Ginkgo* Tea Mixture was piled at 25° C. and 50% relative humidity for 2 hours. 520 g of the mixture was steamed for 10 seconds. The spores of *Eurotium cristatum* (2.5 g, $1\times10^6$/g powder) were dusted onto the Fermented Lilac *Ginkgo* Tea Mixture. The Fermented Lilac *Ginkgo* Tea Mixture was pressed into brick shape in a press mold. After cooling down, the Fermented Lilac *Ginkgo* Tea Mixture was cured in a curing room under the following conditions: days 1-4, at 22° C. and 75% relative humidity; days 5-8, at 25° C. and 65% relative humidity; days 9-14, at 28° C., relative humidity changing every 2 days (days 9-10, 60%; days 11-12, 55%; days 13-14, 45%). After curing, the mixture was slowly dried in a dry and ventilated environment, and the water content of the mixture was reduced to about 7%. 400 g of Lilac *Ginkgo* Brick Tea was obtained.

Example 2

Fresh Lilac leaves and *Ginkgo* leaves were immersed in mountain spring water, rinsed 3 times, drained and placed in bamboo rafts (about 3 cm thick), dried in a cool dry place for 6 hours, placed in a slicer, cut into 4 mm strips. The Lilac leaves were dried in a tea dryer at 130° C. for 6 minutes. Fixation of the Lilac leaves was complete, and the water content was about 55%. The *Ginkgo* leaves were dried in a tea dryer at 220° C. for 11 minutes. The Lilac leaves and *Ginkgo* leaves were then mixed in a weight ratio of 7:3, rolled in a tea roller for 40 minutes, and dried in a tea dryer at 115° C. for 3 hours to make the Lilac *Ginkgo* Tea.

The Lilac *Ginkgo* Tea was piled to remove bitterness. The spores of *Eurotium cristatum* ($1\times10^6$/mL suspension) were sprayed onto the Lilac *Ginkgo* Tea in a ratio of 5 mL suspension per kilogram of the Lilac *Ginkgo* Tea and mixed well (water content: about 55%). The Lilac *Ginkgo* Tea was piled at 35° C. and 85% relative humidity for 30 hours and dried in a tea dryer at 115° C. for 4 hours to prepare a Fermented Lilac *Ginkgo* Tea.

Black tea (60 kg) and Fermented Lilac *Ginkgo* Tea (40 kg) were mixed to make Fermented Lilac *Ginkgo* Tea Mixture (100 kg). 1 kg of Fermented Lilac *Ginkgo* Tea Mixture was added to 35 kg river water, boiled for 30 min, and filtered and cooled to obtain an extract. 30 kg of extract was added to the remaining Fermented Lilac *Ginkgo* Tea Mixture. The Fermented Lilac *Ginkgo* Tea Mixture was piled at 20° C. and 45% relative humidity for 3 hours. 520 g of the mixture was steamed for 8 seconds. The spores of *Eurotium cristatum* (1.5 g, $1\times10^6$/g powder) were dusted onto the Fermented Lilac *Ginkgo* Tea Mixture. The Fermented Lilac *Ginkgo* Tea Mixture was pressed into brick shape in a press mold. After cooling down, the Fermented Lilac *Ginkgo* Tea Mixture was cured in a curing room under the following conditions: days 1-4, at 25° C. and 80% relative humidity; days 5-8, at 26° C. and 65% relative humidity; days 9-14, at 29° C., relative humidity changing every 2 days (days 9-10, 60%; days 11-12, 55%; days 13-14, 45%). After curing, the mixture was slowly dried in a dry and ventilated environment, and the water content of the mixture was reduced to about 7%. 400 g of Lilac *Ginkgo* Brick Tea was obtained.

Example 3

Fresh Lilac leaves and *Ginkgo* leaves were immersed in mountain spring water, rinsed 2 times, drained and placed in bamboo rafts (about 1.5 cm thick), dried in a cool dry place for 3 hours, placed in a slicer, cut into 5 mm strips. The Lilac leaves were dried in a tea dryer at 150° C. for 4 minutes. Fixation of the Lilac leaves was complete, and the water content was about 40%. The *Ginkgo* leaves were dried in a tea dryer at 250° C. for 12 minutes. The Lilac leaves and *Ginkgo* leaves were then mixed in a weight ratio of 7:3, rolled in a tea roller for 20 minutes, and dried in a tea dryer at 120° C. for 1 hour to make the Lilac *Ginkgo* Tea.

The Lilac *Ginkgo* Tea was piled to remove bitterness. The spores of *Eurotium cristatum* ($1\times10^6$/mL suspension) were sprayed onto the Lilac *Ginkgo* Tea in a ratio of 7 mL suspension per kilogram of the Lilac *Ginkgo* Tea and mixed well (water content: about 55%). The Lilac *Ginkgo* Tea was piled at 25° C. and 65% relative humidity for 40 hours and dried in a tea dryer at 120° C. for 2 hours to prepare a Fermented Lilac *Ginkgo* Tea.

Black tea (10 kg) and Fermented Lilac *Ginkgo* Tea (90 kg) were mixed to make Fermented Lilac *Ginkgo* Tea Mixture (100 kg). 1 kg of Fermented Lilac *Ginkgo* Tea Mixture was added to 45 kg river water, boiled for 30 min, and filtered and cooled to obtain an extract. 35 kg of extract was added to the remaining Fermented Lilac *Ginkgo* Tea Mixture. The Fermented Lilac *Ginkgo* Tea Mixture was piled at 30° C. and 60% relative humidity for 1 hour. 520 g of the mixture was steamed for 12 seconds. The spores of *Eurotium cristatum* (3.0 g, $1\times10^6$/g powder) were dusted onto the Fermented Lilac *Ginkgo* Tea Mixture. The Fermented Lilac *Ginkgo* Tea Mixture was pressed into brick shape in a press mold. After cooling down, the Fermented Lilac *Ginkgo* Tea Mixture was cured in a curing room under the following conditions: days 1-4, at 20° C. and 65% relative humidity; days 5-8, at 27° C. and 65% relative humidity; days 9-14, at 28° C., relative humidity changing every 2 days (days 9-10, 60%; days 11-12, 55%; days 13-14, 45%). After curing, the mixture was slowly dried in a dry and ventilated environment, and the water content of the mixture was reduced to about 7%. 400 g of Lilac *Ginkgo* Brick Tea was obtained.

Example 4

Fresh Lilac leaves and *Ginkgo* leaves were immersed in mountain spring water, rinsed 3 times, drained and placed in bamboo rafts (about 1.5 cm thick), dried in a cool dry place for 5 hours, placed in a slicer, cut into 4 mm strips. The Lilac leaves were dried in a tea dryer at 135° C. for 7 minutes. Fixation of the Lilac leaves was complete, and the water content was about 50%. The *Ginkgo* leaves were dried in a tea dryer at 230° C. for 15 minutes. The Lilac leaves and *Ginkgo* leaves were then mixed in a weight ratio of 7:3, rolled in a tea roller for 35 minutes, and dried in a tea dryer at 115° C. for 2 hours to make the Lilac *Ginkgo* Tea.

The Lilac *Ginkgo* Tea was piled to remove bitterness. The spores of *Eurotium cristatum* ($1\times10^6$/g powder) were dusted onto the Lilac *Ginkgo* Tea in a ratio of 8.0 g of powder per kilogram of the Lilac *Ginkgo* Tea and mixed well (water content: about 45%). The Lilac *Ginkgo* Tea was piled at 30° C. and 75% relative humidity for 30 hours and dried in a tea dryer at 110° C. for 5 hours to prepare a Fermented Lilac *Ginkgo* Tea.

Black tea (40 kg) and Fermented Lilac *Ginkgo* Tea (60 kg) were mixed to make Fermented Lilac *Ginkgo* Tea Mixture (100 kg). 1 kg of Fermented Lilac *Ginkgo* Tea Mixture was added to 65 kg river water, boiled for 30 min, and filtered and cooled to obtain an extract. 40 kg of extract was added to the remaining Fermented Lilac *Ginkgo* Tea Mixture. The Fermented Lilac *Ginkgo* Tea Mixture was piled at 25° C. and 55% relative humidity for 2 hours. 520 g of the mixture was steamed for 11 seconds. The spores of *Eurotium cristatum* (2 mL, $1\times10^6$/mL suspension) were sprayed onto the Fermented Lilac *Ginkgo* Tea Mixture. The Fermented Lilac *Ginkgo* Tea Mixture was pressed into brick shape in a press mold. After cooling down, the Fermented Lilac *Ginkgo* Tea Mixture was cured in a curing room under the following conditions: days 1-4, at 24° C. and 70% relative humidity; days 5-8, at 25° C. and 65% relative humidity; days 9-14, at 30° C., relative humidity changing every 2 days (days 9-10, 60%; days 11-12, 55%; days 13-14, 45%). After curing, the mixture was slowly dried in a dry and ventilated environment, and the water content of the mixture was reduced to about 7%. 400 g of Lilac *Ginkgo* Brick Tea was obtained.

Example 5

Lilac *Ginkgo* Brick Tea Reducing Lipid in Animal Experiment

The lipid-lowering effect of the Lilac *Ginkgo* Brick Tea of Example 1 on hyperlipidemia mice:

Male Kunming mice, SPF grade, five weeks old, 30-35 g, were fed with high-fat diet for 24 days, and fasted for 12 hours. Mouse blood was collected from the tail vein. The serum levels of TC and TG were determined to confirm that the hyperlipidemia mouse model was established. 100 g of Lilac *Ginkgo* Brick Tea was boiled in 1 L water, filtered, and concentrated to 50 mL concentrated Lilac *Ginkgo* Brick Tea solution. 30 hyperlipidemia mice were randomly divided into Control Group, Low Dosage Group, and High Dosage Group, 10 mice each group. Blank Group (normal, non-hyperlipidemia mice) was given water and fed with regular food. Control Group was given water and fed with high-fat food. Low Dosage Group and High Dosage Group were given 20 mL/kg/day and 50 mL/kg/day of concentrated Lilac *Ginkgo* Brick Tea solution, respectively, and fed with high-fat food. After 24 days, blood samples were taken, and serum triglyceride (TG), total cholesterol (TC), low-density lipoprotein cholesterol (LDL-C), high density lipoprotein cholesterol (HDL-C) levels were measured and shown in Table 2.

TABLE 2

| Groups | TC/ (mmol · L$^{-1}$) | TG/ (mmol · L$^{-1}$) | LDL-C/ (mmol · L$^{-1}$) | HDL-C/ (mmol · L$^{-1}$) |
| --- | --- | --- | --- | --- |
| Blank | 1.84 ± 0.20 | 0.79 ± 0.18 | 0.47 ± 0.15 | 1.25 ± 0.49 |
| Control | 3.99 ± 0.65 | 1.36 ± 0.35 | 1.75 ± 0.53 | 0.85 ± 0.16 |
| Low Dosage | 3.01 ± 0.49 | 1.12 ± 0.27 | 1.36 ± 0.33 | 1.04 ± 0.32 |
| High Dosage | 2.35 ± 0.58 | 0.97 ± 0.25 | 1.01 ± 0.37 | 1.17 ± 0.22 |

As shown in Table 2, the TC, TG, and LDL-C levels in the Control group significantly increased, and HDL-C level significantly decreased. These results indicated that hyperlipidemia mouse model was established. The TC, TG, and LDL-C levels in both Low Dosage and High Dosage Groups were significantly lower than those in the Control Group. The HDL-C lever in in both Low Dosage and High Dosage Groups was higher than the level in the Control Group. This indicates that the clove *Ginkgo biloba* brick group can significantly improve the blood lipid level of mice, thereby reducing the risk of arteriosclerosis.

Example 6

Lilac *Ginkgo* Brick Tea Protecting Liver in Animal Experiment

To study the liver protection effect of the Lilac *Ginkgo* Brick Tea of Example 1, the following experiments were conduct.

Male Kunming mice, 50 SPF grades, 5 weeks old, 30-35 g, were randomly divided into Blank Group, Control Group, Tiopronin Positive Control Group, Low Dosage Group, and High Dosage Group. 100 g of Lilac *Ginkgo* Brick Tea was boiled in 1 L water, filtered, and concentrated to 50 mL concentrated Lilac *Ginkgo* Brick Tea solution. Blank Group and Control Group were given water and regular food; Tiopronin Group was given 50 mg/kg/day Tiopronin; and Low Dosage Group and High Dosage Group were given 20 mL/kg/day and 50 mL/kg/day concentrated Lilac *Ginkgo* Brick Tea solution, respectively, and regular food. Control Group, Tiopronin Positive Control Group, Low Dosage Group, and High Dosage Group were given 3 g/kg/day (0.01 mL/g) ethanol alcohol. Blank Group was given equal volume water. After 25 days, the mice were fasted for 2 hours, and blood samples were taken to determine alanine aminotransferase (ALT), aspartate aminotransferase (AST), and triglyceride (TG) levels. The results are shown in Table 3.

TABLE 3

| Groups | ALT (U/L) | AST (U/L) | TG (mmol/L) |
| --- | --- | --- | --- |
| Blank | 54.97 ± 9.75 | 134.50 ± 19.54 | 0.915 ± 0.17 |
| Control | 74.96 ± 14.62 | 173.51 ± 13.95 | 2.045 ± 0.38 |
| Tiopronin | 64.80 ± 10.47 | 140.39 ± 20.92 | 1.295 ± 0.43 |
| High dosage | 57.95 ± 2.67 | 135.67 ± 5.57 | 0.824 ± 0.45 |
| Low dosage | 59.94 ± 9.54 | 137.84 ± 21.95 | 0.900 ± 0.20 |

As shown in Table 3, both low dose and high dose of the Lilac *Ginkgo* Brick Tea solution can significantly reduce ALT, AST and TG levels in the mouse serum. This indicates that Lilac *Ginkgo* Brick Tea can protect the liver from alcohol's damage.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of preparing a Lilac *Ginkgo* Brick Tea consisting of the following steps:
    (1) mixing and drying fresh Lilac leaves and *Ginkgo* leaves to obtain a Lilac *Ginkgo* Tea;
    (2) fermenting the Lilac *Ginkgo* Tea to obtain a Fermented Lilac *Ginkgo* Tea;
    (3) mixing the Fermented Lilac *Ginkgo* Tea with a black tea to obtain a Fermented Lilac *Ginkgo* Tea Mixture; and
    (4) processing the Fermented Lilac *Ginkgo* Tea Mixture to obtain the Lilac *Ginkgo* Brick Tea,
    wherein step (1) mixing and drying fresh Lilac leaves and *Ginkgo* leaves consists of:
        collecting fresh Lilac leaves and *Ginkgo* leaves in a weight ratio of 7:3;

washing the Lilac leaves and the *Ginkgo* leaves with water 2-3 times;

drying the Lilac leaves and the *Ginkgo* leaves at room temperature for 3-6 hours;

cutting the Lilac leaves and the *Ginkgo* leaves into strips with a width of 3-5 mm;

drying the Lilac leaves at 130-150° C. for 4-7 minutes, rolling the Lilac leaves for 20-40 minutes, and drying the Lilac leaves at 110-120° C. for 1-3 hours;

drying the *Ginkgo* leaves at 220-250° C. for 10-15 minutes, rolling the *Ginkgo* leaves for 20-40 minutes, and drying the *Ginkgo* leaves at 110-120° C. for 1-3 hours; and mixing the Lilac leaves and the *Ginkgo* leaves, wherein step (2) fermenting the Lilac *Ginkgo* Tea consists of:

spraying spores of *Eurotium cristatum* onto the Lilac *Ginkgo* Tea in a ratio of $0.5 \times 10^7$-$1 \times 10^7$ spores per kilogram of the Lilac *Ginkgo* Tea;

piling the Lilac *Ginkgo* Tea at 20-30° C. and 65-85% relative humidity for 30-40 hours; and drying the Lilac *Ginkgo* Tea at 20-30° C. for 2-5 hours, wherein in step (3), the Fermented Lilac *Ginkgo* Tea has a weight ratio of 40-90% and the black tea has a weight ratio of 10-60% based on a total weight of the Fermented Lilac *Ginkgo* Tea and the black tea, and wherein step (4) processing the Fermented Lilac *Ginkgo* Tea Mixture consists of:

taking a portion of the Fermented Lilac *Ginkgo* Tea Mixture, boiling in water to obtain an extract;

adding the extract to the remaining Fermented Lilac *Ginkgo* Tea Mixture;

piling the Fermented Lilac *Ginkgo* Tea Mixture at 20-30° C. and 40-60% relative humidity for 1-3 hours;

steaming the Fermented Lilac *Ginkgo* Tea Mixture for 8-12 seconds;

spreading the spores of *Eurotium cristatum* in a ratio of $3 \times 10^6$-$6 \times 10^6$ spores per kilogram of the Fermented Lilac *Ginkgo* Tea Mixture;

pressing the Fermented Lilac *Ginkgo* Tea Mixture into brick shape; and curing the Fermented Lilac *Ginkgo* Tea Mixture at 20-25° C. and 65-80% relative humidity for 4 days and at 25-30° C. and 45-65% relative humidity for 10 days.

* * * * *